United States Patent [19]
Pommer et al.

[11] 3,973,018
[45] Aug. 3, 1976

[54] FUNGICIDE

[75] Inventors: Ernst-Heinrich Pommer; Juergen Kradel, both of Limburgerhof; Karl-Heinz Koenig, Frankenthal; Walter Sanne, Limburgerhof, all of Germany

[73] Assignee: BASF Aktiengesellschaft, Ludwigshafen (Rhine), Germany

[22] Filed: Apr. 3, 1974

[21] Appl. No.: 457,580

[30] Foreign Application Priority Data
Apr. 17, 1973 Germany............................ 2319362

[52] U.S. Cl.............................. 424/248; 424/286; 424/287; 424/289; 424/300
[51] Int. Cl.² ...................... A01N 9/00; A01N 9/12; A01N 9/20; A01N 9/22
[58] Field of Search ........... 424/248, 300, 287, 289, 424/286

[56] References Cited
UNITED STATES PATENTS
2,504,404   4/1950   Flanner.............................. 424/286
3,468,885   9/1969   Sanne et al...................... 260/247.2

FOREIGN PATENTS OR APPLICATIONS
1,164,152   9/1964   Germany

OTHER PUBLICATIONS
Pesticide Index—4th Ed., D. Frear—College Sci. Publi., pp. 221 and 394, (1969).

*Primary Examiner*—Albert T. Meyers
*Assistant Examiner*—D. W. Robinson
*Attorney, Agent, or Firm*—Johnston, Keil, Thompson & Shurtleff

[57] ABSTRACT

A fungicidal composition comprising N-tridecyl-2,6-dimethylmorpholine in combination with a compound selected from the group consisting of manganese ethylenebisdithiocarbamate, manganese zinc ethylenediaminebisdithiocarbamate and an ammonia complex of zinc-(N,N alkylenebisdithiocarbamate) and N,N'-polyethylene bis-(thiocarbamoyl)-disulfide which has a strong synergistic fungicidal action, and a process for controlling the spread of fungi, i.e. inhibiting the growth of fungi, with this composition.

12 Claims, No Drawings

FUNGICIDE

The present invention relates to a fungicide containing a composition of different active ingredients.

It is known to use N-tridecyl-2,6-dimethylmorpholine (German Patent No. 1,164,152) and dithiocarbamates (U.S. Pat. No. 2,504,404) as fungicides.

We have now found that a fungicide containing a composition of
a. N-tridecyl-2,6-dimethylmorpholine and
b. a dithiocarbamate selected from the group consisting of
  manganese ethylenebisdithiocarbamate (maneb);
  manganese zinc ethylenediaminebisdithiocarbamate (mancozeb);
  zinc ethylenebisdithiocarbamate (zineb);
  zinc-(N,N'-propylenebisdithiocarbamate) (propineb);
  ammonia complex of zinc-(N,N'-ethylenebisdithiocarbamate) and N,N'-polyethylenebis-(thiocarbamoyl)-disulfide (metiram); and
  ammonia complex of zinc-(N,N'-propylenebisdithiocarbamate) and N,N'-polypropylenebis-(thiocarbamoyl)-disulfide (methyl metiram)

has a much better fungicidal action than its individual components.

The fungicides of the invention are in particular suitable for controlling plant diseases such as *Puccinia striiformis* (yellow rust) in wheat, *Puccinia hordei* (brown rust) in barley, *Erysiphe graminis* (powdery mildew) in cereals, *Erysiphe cichoriacearum* (powdery mildew) in Cucurbitaceae, *Helminthosporium sativum* (leaf stripe) in barley, *Helminthosporium gramineum* in cereals, *Rhynchosporium secalis* in cereals, *Cercospora herpotrichoides* (eyespot) in cereals, *Fusarium nivale* (snow mold) in wheat and rye, *Fusarium culmorum* in wheat, *Rhizoctonia solani* and *Corticium salmonicolor* in rubber plants, *Botrytis cinerea* in strawberries and ornamentals, *Mycosphaerella musicola* (Sigatoka disease) in bananas, and *Penicillium expansum* and *Penicillium digitatum* in citrus fruits.

The ratio of the active ingredients to each other may vary considerably; it is however preferred to use a ratio by weight of a:b of from 2:1 to 1:4, especially from 1:3 to 1:4.

When the compositions of the invention are used for treating plants, application rates are from 0.5 to 5 kg per hectare. For the surface protection of trees or fruit the compositions may also be used in admixture with plastics dispersions in amounts of from 0.25 to 5%, with reference to the weight of the dispersion.

Application may be effected for instance in the form of directly sprayable solutions, powders, suspensions, dispersions, emulsions, oil dispersions, pastes, dusts, or granules by spraying, atomizing, dusting, broadcasting or watering. The form of application depends entirely on the purpose for which the agents are being used; in any case it should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils and oils of vegetable or mineral origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanine, chlorobenzene, isophorone, etc., and strongly polar solvents such as dimethylformamide and dimethyl sulfoxide are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnpahthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

There may be added to the compositions or individual active ingredients oils of various types, other fungicides, herbicides, nematocides, insecticides, bactericides, trace elements, fertilizers, antifoams (e.g., silicones), growth regulators and other compounds.

The agents may be added to the active ingredients of the invention in a ratio by weight of from 1:10 to 10:1. The same applies to oils, fungicides, nematocides, insecticides, bactericides, trace elements, fertilizers, antifoams and growth regulators.

EXAMPLE 1

Botrytis test 20 ml of a nutrient solution consisting of grapejuice and water in a weight ratio of 1:1 was poured into 100 ml Erlenmeyer flasks. The active ingredients and compositions thereof listed in the table below were then introduced into the flasks. The solutions were subsequently inoculated with conidia of Botrytis cinerea (gray mold). After an incubation period of 5 days at 22° to 23°C the extent of fungus spread on the surface of the nutrient solution was assessed in accordance with the following ratings.
0 = no fungus growth
1 = odd fungus colonies
2 = 5 to 10% of surface covered by fungus
3 = 10 to 30% of surface covered by fungus
4 = 30 to 60% of surface covered by fungus
5 = 60 to 100% of surface covered by fungus fungus spread on the surface of the nutrient solution was assessed in accordance with the following ratings:
0 = no fungus growth
1 = odd fungus colonies
2 = 5 to 10% of surface covered by fungus; odd colonies in the nutrient solution
3 = 10 to 30% of surface covered by fungus; numerous colonies in the nutrient solution
4 = 30 to 60% of surface covered by fungus; coherent mycelium in the nutrient solution
5 = 60 to 100% of surface covered by fungus; ex-

| Active ingredient | Ratio | Amount of active ingredient in nutrient solution in parts by weight of active ingredient or active ingredient composition per million parts of nutrient solution | | | | | |
|---|---|---|---|---|---|---|---|
| | | 40 | 20 | 15 | 10 | 5 | 2.5 |
| N-tridecyl-2,6-dimethylmorpholine | — | 1 | 2 | 3 | 3 | 4 | 5 |
| Maneb | — | 1 | 2 | 2 | 4 | 5 | 5 |
| Mancozeb | — | 2 | 3 | 3 | 5 | 5 | 5 |
| Zineb | — | 5 | 5 | 5 | 5 | 5 | 5 |
| Propineb | — | 3 | 3 | 5 | 5 | 5 | 5 |
| Metiram | — | 4 | 5 | 5 | 5 | 5 | 5 |
| Methyl-metiram | — | 3 | 4 | 5 | 5 | 5 | 5 |
| N-tridecyl-2,6-dimethylmorpholine + Maneb | 1:1 | 0 | 0 | 1 | 1 | 2 | |
| | 1:2 | 0 | 0 | 1 | 2 | 2 | |
| | 1:3 | 0 | 0 | 1 | 2 | 3 | |
| | 1:4 | 0 | 0 | 1 | 2 | 3 | |
| N-tridecyl-2,6-dimethylmorpholine + Mancozeb | 1:1 | 0 | 1 | 1 | 2 | 3 | |
| | 1:2 | 0 | 1 | 2 | 2 | 3 | |
| | 1:3 | 0 | 1 | 2 | 2 | 4 | |
| | 1:4 | 0 | 1 | 2 | 2 | 4 | |
| N-tridecyl-2,6-dimethylmorpholine + Zineb | 1:1 | 0 | 0 | 1 | 2 | 3 | |
| | 1:2 | 0 | 1 | 2 | 2 | 3 | |
| | 1:3 | 1 | 1 | 2 | 2 | 4 | |
| N-tridecyl-2,6-dimethylmorpholine + Propineb | 1:1 | 0 | 0 | 1 | 2 | 3 | |
| | 1:2 | 0 | 0 | 1 | 3 | 4 | |
| | 1:3 | 0 | 1 | 2 | 3 | 4 | |
| | 1:4 | 0 | 1 | 3 | 3 | 4 | |
| N-tridecyl-2,6-dimethylmorpholine + Metiram | 2:1 | 0 | 0 | 1 | 1 | 2 | |
| | 1:1 | 0 | 0 | 1 | 1 | 2 | |
| | 1:2 | 0 | 1 | 1 | 2 | 3 | |
| | 1:3 | 0 | 1 | 2 | 2 | 3 | |
| | 1:4 | 0 | 1 | 2 | 3 | 4 | |
| N-tridecyl-2,6-dimethylmorpholine + Methyl-metiram | 1:1 | 0 | 0 | 1 | 1 | 2 | |
| | 1:2 | 0 | 1 | 1 | 1 | 2 | |
| | 1:3 | 0 | 1 | 2 | 2 | 3 | |
| | 1:4 | 1 | 1 | 2 | 2 | 4 | |
| Control (untreated) | | | | | 5 | | |

EXAMPLE 2 tremely vigorous mycelium growth in the nutrient solution.

| Active ingredient | Ratio | Amount of active ingredient in nutrient solution in parts by weight of active ingredient or active ingredient composition per million parts of nutrient solution | | |
|---|---|---|---|---|
| | | 40 | 20 | 10 |
| N-tridecyl-2,6-dimethylmorpholine | — | 4 | 5 | 5 |
| Maneb | — | 4 | 5 | 5 |
| Metiram | — | 4 | 5 | 5 |
| N-tridecyl-2,6-dimethylmorpholine + maneb | 2:1 | 1 | 1 | 2 |
| | 1:1 | 1 | 1 | 1 |
| | 1:2 | 1 | 2 | 2 |
| | 1:3 | 1 | 2 | 3 |
| N-tridecyl-2,6-dimethylmorpholine + metiram | 2:1 | 1 | 2 | 3 |
| | 1:1 | 1 | 2 | 3 |
| | 1:2 | 2 | 3 | 3 |
| Control (untreated) | — | | 5 | |

Rhizoctonia solani test 20 ml of a solution containing 5% of a malt nutrient was poured into 100 ml Erlenmeyer flasks. The active ingredients and compositions thereof listed in the table below were then introduced into the flasks. The solutions were subsequently inoculated with mycelium flakes of the fungus *Rhizoctonia solani*. After an incubation period of 8 days at 22° to 23°C the extent of

EXAMPLE 3

Fusarium nivale test 20 ml of a solution containing 5% of a malt nutrient was poured into 100 ml Erlenmeyer flasks. The active ingredients and compositions thereof listed in the table below were then introduced into the flasks. The solutions were subsequently inoculated with spores of snow mold (*Fusarium nivale*). After an incubation period of 8 days at 22° to 23°C the extent of fungus spread on the surface of, and in, the nutrient solution was assessed in accordance with the following ratings:

- 0 = no fungus growth
- 1 = odd fungus colonies
- 2 = 5 to 10% of surface covered by fungus; odd colonies in the nutrient solution
- 3 = 10 to 30% of surface covered by fungus; numerous colonies in the nutrient solution
- 4 = 30 to 60% of surface covered by fungus; coherent mycelium in the nutrient solution
- 5 = 60 to 100% of surface covered by fungus; extremely vigorous mycelium growth in the nutrient solution.

| Active ingredient | Ratio | Amount of active ingredient in nutrient solution in parts by weight of active ingredient or active ingredient composition per million parts of nutrient solution | | | |
|---|---|---|---|---|---|
| | | 40 | 20 | 10 | 5 |
| N-tridecyl-2,6-dimethylmorpholine | — | 4 | 4 | 5 | 5 |
| Maneb | — | 2 | 2 | 4 | 5 |
| N-tridecyl-2,6-dimethylmorpholine + maneb | 2:1 | 1 | 1 | 2 | 3 |
| | 1:1 | 1 | 1 | 2 | 2 |
| | 1:2 | 1 | 1 | 2 | 3 |
| | 1:3 | 1 | 1 | 2 | 2 |
| | 1:4 | 1 | 1 | 1 | 1 |
| Control (untreated) | — | | | 5 | |

We claim:

1. A synergistic fungicidal composition consisting essentially of
   a. N-tridecyl-2,6-dimethylmorpholine and
   b. manganese zinc ethylenediaminebisdithiocarbamate, the ratio by weight of a:b being from 2:1 to 1:4.

2. A fungicidal composition as claimed in claim 1 wherein the ratio by weight of a:b is 1:3 to 1:4.

3. A synergistic fungicidal composition consisting essentially of (a) N-tridecyl-2,6-dimethylmorpholine and (b) manganese ethylenebisdithiocarbamate, the ratio by weight of a:b being from 2:1 to 1:4.

4. A fungicidal composition as claimed in claim 3 wherein the ratio by weight of a:b is 1:3 to 1:4.

5. A synergistic fungicidal composition consisting essentially of
   a. N-tridecyl-2,6-dimethylmorpholine and
   b. ammonia complex of zinc-(N,N'-ethylenebisdithiocarbamate) and N,N'-polyethylenebis-(thiocarbamoyl)-disulfide, the ratio by weight of a:b being from 2:1 to 1:4.

6. A fungicidal composition as claimed in claim 5 wherein the ratio by weight of a:b is 1:3 to 1:4.

7. A process for inhibiting the growth of fungi which comprises applying to the plants suffering fungus attack or to be protected against fungus attack a fungicidal amount of a synergistic composition consisting essentially of:
   a. N-tridecyl-2,6-dimethylmorpholine and
   b. manganese zinc ethylenediamine bisdithiocarbamate, the ratio by weight of a:b being from 2:1 to 1:4.

8. The process of claim 7 wherein the ratio by weight of a:b is 1:3 to 1:4.

9. A process for inhibiting the growth of fungi which comprises applying to the plants suffering fungus attack or to be protected against fungus attack a fungicidal amount of a synergistic composition consisting essentially of
   a. N-tridecyl-2,6-dimethylmorpholine and
   b. manganese ethylenebisdithiocarbamate, the ratio by weight of a:b being from 2:1 to 1:4.

10. The process of claim 9 wherein the ratio by weight of a:b is 1:3 to 1:4.

11. A process for inhibiting the growth of fungi which comprises applying to the plants suffering fungus attack or to be protected against fungus attack a fungicidal amount of a synergistic composition consisting essentially of
    a. N-tridecyl-2,6-dimethylmorpholine and
    b. ammonia complex of zinc-(N,N'-ethylenebisdithiocarbamate) and N,N'-polyethylenebis-(thiocarbamoyl)-disulfide, the ratio by weight of a:b being from 2:1 to 1:4.

12. The process of claim 11 wherein the ratio by weight of a:b is 1:3 to 1:4.

* * * * *